United States Patent [19]

Grüning et al.

[11] Patent Number: 4,988,806
[45] Date of Patent: Jan. 29, 1991

[54] NITROGEN-CONTAINING DERIVATIVES OF CARBOXYMETHYLCELLULOSE, THEIR SYNTHESIS AND THEIR USE IN COSMETIC PREPARATIONS

[75] Inventors: Burghard Grüning; Klaus Hoffmann; Götz Koerner; Hans-Joachim Kollmeier, all of Essen, Fed. Rep. of Germany

[73] Assignee: Th. Goldschmidt AG, Essen, Fed. Rep. of Germany

[21] Appl. No.: 365,612

[22] Filed: Jun. 13, 1989

[30] Foreign Application Priority Data

Jun. 13, 1988 [DE] Fed. Rep. of Germany ....... 3820031

[51] Int. Cl.$^5$ .................. C08B 11/12; C08B 3/00; A61K 7/06; A61K 7/09
[52] U.S. Cl. .................... 536/98; 536/30; 536/32; 536/58; 536/63; 424/70; 424/71; 514/781; 514/880
[58] Field of Search ............. 536/30, 32, 58, 63, 536/98; 424/DIG. 2, 70, 71; 514/781, 880

[56] References Cited

U.S. PATENT DOCUMENTS

| | | | |
|---|---|---|---|
| 4,180,084 | 12/1979 | Wegmüller et al. | 132/203 |
| 4,197,865 | 4/1980 | Jacquet et al. | 132/204 |
| 4,213,960 | 7/1980 | Grollier et al. | 424/47 |

FOREIGN PATENT DOCUMENTS

| | | |
|---|---|---|
| 0189935 | 6/1986 | European Pat. Off. |
| 3301667 | 10/1970 | Fed. Rep. of Germany |
| 1593657 | 7/1984 | Fed. Rep. of Germany |
| 3502833 | 7/1986 | Fed. Rep. of Germany |
| 49-18981 | 2/1974 | Japan |

Primary Examiner—Merrell C. Cashion, Jr.
Assistant Examiner—G. S. Kishore
Attorney, Agent, or Firm—Toren, McGeady & Associates

[57] ABSTRACT

Derivatives of carboxymethylcellulose are disclosed in which all or a portion of the carboxymethyl groups are replaced by groups of the general formula

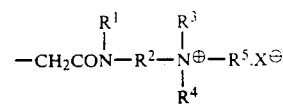

in which
$R^1$ is a hydrogen or methyl group,
$R^2$ is a divalent aliphatic hydrocarbon group with 2 to 5 carbon atoms,
$R^3$, $R^4$ are alkyl groups with 1 to 4 carbon atoms,
$R^5$ is an alkyl group with 1 to 4 carbon atoms or a benzyl group,
X is a halogen or sulfate group or a sulfonic acid group, with the proviso that, on the average, at least 0.1 quaternary ammonium groups are contained per anhydroglucose unit of the polymeric molecule.

The invention furthermore relates to derivatives of carboxymethylcellulose, in which all or a portion of the carboxymethyl groups are replaced by groups of the general formula

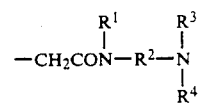

in which the substituents $R^1$, $R^2$, $R^3$ and $R^4$ have the above meaning, with the proviso that, on the average, at least 0.1 tertiary amino groups are contained per anhydroglucose unit of the polymeric molecule, as intermediates for the synthesis of the aforementioned derivatives.

The invention furthermore is directed to a method for the synthesis of the derivatives of carboxymethylcellulose and their use in cosmetic preparations, especially for the care of hair.

12 Claims, No Drawings

NITROGEN-CONTAINING DERIVATIVES OF CARBOXYMETHYLCELLULOSE, THEIR SYNTHESIS AND THEIR USE IN COSMETIC PREPARATIONS

FIELD OF INVENTION

The invention is directed to derivatives of carboxymethylcellulose with quaternary ammonium groups as well as to a method for the synthesis of these compounds and their use in cosmetic preparations, especially for the care of hair. The invention furthermore is directed to derivatives of carboxymethylcellulose with tertiary amino groups as intermediates for the synthesis of the derivatives of carboxymethylcellulose.

BACKGROUND INFORMATION AND PRIOR ART

The German Patent No. 1,593,657 discloses quaternary nitrogen-containing cellulose ethers, which correspond to the structural formula

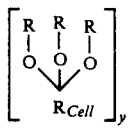

in which $R_{Cell}$ represents an anhydroglucose unit, y is a whole number from 200 to 5,000 and each R group represents a substituent of the following general formula:

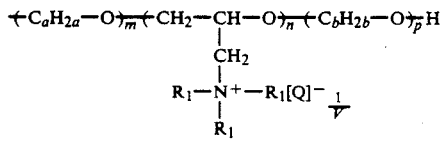

in which "a" and "b" are 2 or 3, m and p are whole numbers from 0 to 10, n is a whole number from 0 to 3, $R_1$ represents a methyl or ethyl group, Q represents an anion and v is a whole number, which corresponds to the valence of Q. In the above formula, the average value of n per anhydroglucose unit of the cellulose ether is 0.1 to 0.5 and that of m+n+p is 0.1 to 2.5, with the exception of the cellulose ethers, for which the average value of m+p is equal to zero.

According to the claims of the patent, these ethers have an improved substantivity towards different substrates in comparison with unmodified cellulose ethers. They can therefore be used for purposes, for which the conventional cellulose ethers are not or not very suitable because of their nonionic or anionic character. The compounds can be used in cosmetic formulations.

The German Offenlegungsschrift No. 3,301,667 is directed to a method for the synthesis of cationic cellulose derivatives, which is characterized in that (a) an alkali cellulose, suspended in an aqueous organic solvent that is at least partly miscible with water, is reacted with a nonionic etherification agent from the group consisting of glycide, glycide acetate or glycerin chlorohydrin in an amount of 2 to 10 moles/mole of anhydroglycose unit, (b) during or after the reaction, the reaction mixture is reacted with a cationic etherification agent of the general formula

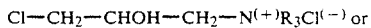

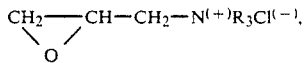

in which R represents a lower alkyl group with 1 to 4 carbon atoms or the group $—N^{(+)}R_3Cl^{(-)}$ is replaced by a group

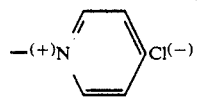

in an amount of 0.5 to 2.0 moles/mole of anhydroglycose unit.

It is pointed out in this Offenlegungsschrift that the known cationic conditioning agents (which also include the products of the German Patent No. 1,593,657) would have numerous deficiencies. For example, products with a good water solubility and a sufficient compatibility with anionic washing raw materials generally are not sufficiently active, so that a high dosage would be required. Other products of limited water solubility are too strongly substantive and are exhausted almost completely on the hair. After several treatments, this would lead to an accumulation and a decrease in the fullness and the set of the dried hair. The products of the German Offenlegungsschrift No. 3,301,667 would have these disadvantages to an appreciably lesser extent, if at all.

The German Offenlegungsschrift No. 3,502,833 discloses a cosmetic agent for the treatment of hair or skin, which contains a quaternary, macromolecular, polymeric compound derived from chitosan. The compounds are synthesized by reacting a chitosan, consisting of 50 to 100% deacetylated chitin, in the presence of a solvent with a glycidyl trialkylammonium halide and ethylene oxide in a suitable ratio. As starting material, especially chitosan, purified by reprecipitation, is used.

In the published European Patent Application No. 0 189 935, water-soluble cationic polysaccharides based on cellulose ethers are described, which differ from the compounds of the German Patent No. 1,593,657 essentially by additionally having an alkyl group with at least 8 carbon atoms. As a result, they are hydrophobically substituted.

OBJECTS OF THE INVENTION

It is an object of the invention to provide nitrogen-containing products based on cellulose, which show improved solubility behavior in water and which have better application properties, especially when used in cosmetic preparations for the hair. The expression, improved solubility behavior in water, is to be understood to mean that, when the products are dissolved in water, gel-like intermediate states are avoided or at least largely excluded. It shall be possible to bring the products into aqueous solution rapidly and without special mechanical aids. The improved cosmetic properties of the novel products shall comprise especially an improvement in the gloss, the handle and/or the compatibility of the hair. The substantivity of the products shall be so balanced, that an accumulation of the active ingredients on the hair is avoided even after repeated application. The compounds shall be such, that they can be synthesized from easily accessible raw materials.

SUMMARY OF THE INVENTION

Surprisingly, it was found that certain derivatives of carboxymethylcellulose satisfy these requirements.

An aspect of the invention thus are derivatives of carboxymethylcellulose with quaternary ammonium groups with the characteristic feature, that all or a portion of the carboxymethyl groups are replaced by groups of the general formula

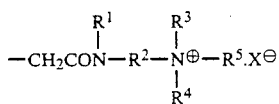

in which
- $R^1$ is a hydrogen or methyl group,
- $R^2$ is a divalent aliphatic hydrocarbon group with 2 to 5 carbon atoms,
- $R^3$, $R^4$ are alkyl groups with 1 to 4 carbon atoms,
- $R^5$ is an alkyl group with 1 to 4 carbon atoms or a benzyl group,
- X is a halogen or sulfate ester group or a sulfonic acid group, with the proviso that, on the average, at least 0.1 quaternary ammonium groups are contained per anhydroglucose unit of the polymeric molecule.

Those derivatives of carboxymethylcellulose are preferred, which contain 0.3 to 0.8 and especially 0.3 to 0.6 quaternary ammonium groups per anhydroglycose unit.

The number of anhydroglucose units in the average polymeric molecule shall be about 400 to 10,000.

In formula I, $R^1$ represents a hydrogen or methyl group. Preferably, $R^1$ is a hydrogen.

$R^2$ is a divalent aliphatic hydrocarbon group with 2 to 5 carbon atoms. This alkylene group optionally may be branched; however, linear alkylene groups and especially those with 2 to 4 carbon atoms are preferred. Examples of such $R^2$ groups are $-CH_2-CH_2-$, $-CH_2-CH_2-CH_2-$ and $$-\underset{\underset{CH_3}{|}}{CH}-CH_2-CH_2-CH_2-\text{ groups.}$$

The $R^3$ and $R^4$ groups may be the same or different and represent alkyl groups with 1 to 4 carbon atoms. The alkyl group is preferred.

$R^5$ is an alkyl group with 1 to 4 carbon atoms or a benzyl group. As alkyl group, the methyl group is preferred.

X is a halogen, sulfate ester or sulfonate group, which is present in anionic form. The halogen and especially the chloro group is preferred. Examples of suitable sulfate ester and sulfonate groups are

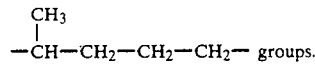

In principle, however, other physiologically safe groups, which are present in anionic form, can also be used, since the properties of the products are affected only slightly, if at all, by the anionic group.

A further aspect of the invention is a method for synthesizing the inventive compounds. This inventive method is carried out in three steps. According to a simplified description of the method, the alkali salts of the carboxymethylcellulose are esterified with alkyl chloride in the first step, the ester obtained is converted into a derivative with tertiary amino groups in the second step and the intermediate obtained is quaternized in the third step.

The inventive method thus is characterized in that (a) an alkali salt of the carboxymethylcellulose is esterified at temperatures of 80° to 170° C., a pressure of 5 to 100 bar and a reaction time of 1 to 24 hours in a known manner with, based on the carboxymethyl groups, a 1- to 10-fold molar excess of alkyl chloride, the alkyl group of which has 1 to 3 carbon atoms, the excess alkyl chloride being removed from the reaction mixture in a known manner after the esterification, (b) the ester of the carboxymethylcellulose, thus obtained, is reacted with amines of the general formula

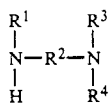

in which $R^1$, $R^2$, $R^3$ and $R^4$ are defined as in Formula I, at temperatures of 80° to 150° C., a reaction time of 1 to 10 hours and optionally at an elevated pressure in such amounts, that 1 to 10 moles of amine are used per mole of ester group. After the reaction, the excess amine is removed from the reaction mixture in a known manner, whereupon (c) the derivative of carboxymethylcellulose, thus obtained, which has tertiary amino group, is reacted optionally at an elevated temperature and optionally at an elevated pressure during a reaction time of 0.5 to 8 hours with, based on the tertiary amino groups, at least equimolar amounts of the compound $R^5-X$, in which $R^5$ and X are as defined in Formula I.

The esterification in the first step is carried out by a known procedure with alkyl chloride, the alkyl group of which has 1 to 3 carbon atoms. Preferably, methyl chloride is used for the esterification. The reaction is carried out at an elevated temperature of 80° to 170° C., a temperature in the range of 80° to 110° C. being preferred. The reaction is carried out at an elevated pressure of 5 to 100 bar and preferably at a pressure of 5 to 50 bar. The reaction is completed within 1 to 24 hours, depending on the alkyl chloride used. Yields as high as about 95% of the theoretical can be achieved. At least equimolar amounts of alkyl chloride are used. It is advisable to use an excess of alkyl chloride; however, for economic reasons, a more than 10-fold excess is avoided. After the reaction, the excess amount of alkyl chloride is removed in a known manner, preferably by distillation.

In the second step, the alkyl ester of the carboxymethylcellulose, thus obtained, is reacted with amines of the general formula

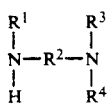

The $R^1$, $R^2$, $R^3$ and $R^4$ groups are defined as above. A reaction temperature, which falls within the range of 80° to 150° C. and preferably within the range of 100° to 140°, is selected. The reaction optionally may be carried out at an elevated pressure; this depends essentially on the boiling point of the amine used. The reaction is concluded within 1 to 10 hours with a yield of about 90%. Per ester group, 1 to 10 moles of the amine are used. The excess amine is removed after the reaction in a known manner. This can be accomplished by filtering the reaction product from the reaction mixture, the precipitation of the reaction product being completed by the addition of polar organic solvents, such as acetone, isopropanol or methanol. Preferably, the reaction is carried in suspension with addition of a inert, polar, organic solvent such as methanol or isopropanol, in a pressure vessel. Preferably, 1 to 3 moles of amine are used for each ester group. Examples of suitable amines of Formula III are

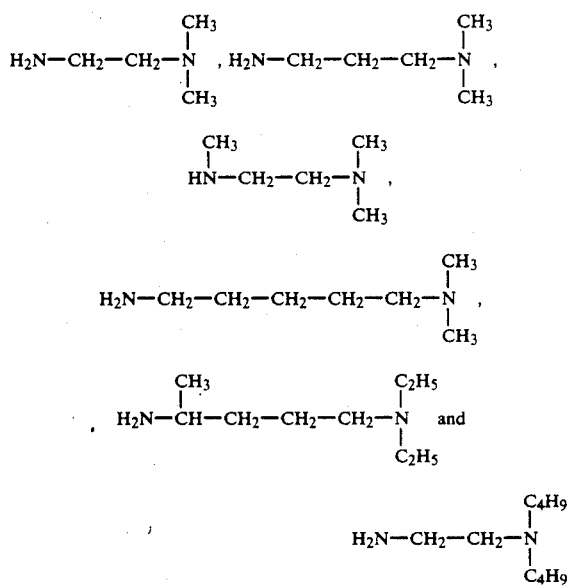

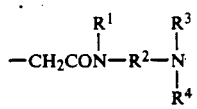

The intermediates obtained in the second step are novel compounds, the properties of which determine the properties of the inventive end products. These novel intermediates, in the form of derivatives of carboxymethylcellulose with tertiary amino groups, therefore are a further aspect of the invention and are characterized in that all or a portion of the carboxymethyl groups are replaced by groups of the general formula $$-CH_2CON-R^2-N\begin{matrix}R^1 & R^3 \\ | & | \\ & \\ & R^4\end{matrix}$$ II in which the substituents $R^1$, $R^2$, $R^3$ and $R^4$ have the above meaning, with the proviso that, on the average, at least 0.1 tertiary amino groups are contained per anhydroglucose unit of the polymeric molecule.

These novel intermediates are now reacted in the third step of the inventive method with, based on the tertiary amino groups, at least equimolar amounts of the compound $R^5$—X. Examples of suitable $R^5$—X compounds are

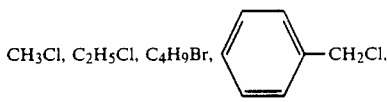

$(CH_3O)_2SO_2$, $(C_2H_5O)_2SO_2$, $CH_3SO_3CH_3$ and

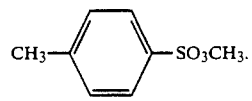

The quaternization reaction is carried out in a known manner. If the boiling point of the compounds $R^5$—X is low, it can optionally be carried out at an elevated pressure. Even though the reaction with methyl chloride, for example, already takes place at 0° C., it is advisable to work at an elevated temperature in order to accelerate the reaction. At the end of the reaction, the excess $R^5$—X portion is removed by distillation or by filtration and washing of the cellulose derivative with a polar organic solvent, such as isopropanol or acetone.

The reaction of step 3 can be carried out in a 2-phase system, the derivative of the carboxymethylcellulose, which is obtained in the second step, being suspended in a suitable liquid, organic phase, such as methanol. A reaction in an aqueous phase is possible; however, because of the high viscosity of the solution, such a reaction is preferred only if the end product is to be used further, directly in the form of an aqueous solution.

Mixed carboxymethyl-hydroxyalkyl-cellulose ethers are also available commercially. They can also be used as starting materials. In this case, the inventive derivatives of the carboxymethylcellulose may additionally contain ether groups, such as $(C_2H_4O)_pH$ and $(C_3H_6O)_pH$, in which p can assume an average value of 1 to 5.

The compounds, synthesized by the inventive method, dissolve in cold or warm water without or largely without forming gelatinous intermediate stages.

A further aspect of the invention is the use of inventive compounds in cosmetic preparation, especially for the care of hair. The inventive compounds meet the requirements listed above particularly well. If hair is treated with aqueous preparations of the inventive compounds, it develops the desired gloss and the pleasant, supple, soft handle and is readily compatible. The products have proven to be useful especially for the care of damaged hair. The inventive compounds shall be contained in the aqueous preparations in an amount of 0.1 to 2.5% by weight. Skin irritations or hair damage have not been observed with the inventive compounds.

The inventive compounds can, moreover, be used to thicken aqueous solutions or aqueous suspensions. They are suitable for the treatment of textile fibers or of yarns produced therefrom or of sheet-like textile fabrics, the improvement in the handle and the decrease in the electrostatic charge once again being a major, characteristic result of the treatment. The inventive compounds can furthermore be added to paper pulp during the manufacture of paper. The compounds can furthermore be used to thicken aqueous vehicles or binders.

In the following examples, the synthesis of inventive compounds of is shown. It should be noted that these examples are given by way of illustration and not by way of limitation. Furthermore, the application properties of the compounds are shown in comparison with those of products of the state of the art.

I. PREPARATION OF INVENTIVE COMPOUNDS

1. Preparation of Carboxymethylcellulose Methyl Ester (Step a) of the Method)

(1 a) As described in the Japanese publication No. 49-18981, 30 g of sodium carboxymethylcellulose, with a degree of modification DS=0.9, a saponification number of less than 4 and a purity of 99.5%, the 1% aqueous solution of which has a Brookfield viscosity of approximately 2,000 mPas, and 87 g of chloromethane are heated for 10 hours at 100° C. in a 250 mL laboratory autoclave. During this time, a pressure of about 40 bar is developed. Subsequently, the chloromethane is evaporated off. To complete the removal of the chloromethane, the product is heated at 60 mbar to 50° C. A total of 34 g of carboxymethylcellulose methyl ester, mixed with the sodium chloride that is formed as a by-product of the reaction, are obtained. The methyl ester has a saponification number of 225, which corresponds to a 90% conversion of the carboxyl groups.

(1 b) In the same way, 30 g of sodium carboxymethylcellulose (sodium salt), with a degree of modification DS of 0.7, a saponification number of less than 4 and a purity of 99.5%, the 1% aqueous solution of which has a Brookfield viscosity of about 1,500 mPas, is reacted with chloromethane. The carboxymethylcellulose methyl ester obtained has saponification number of 200, which corresponds to an 86% conversion of the carboxyl groups.

2. Preparation of the Aminamide of Carboxymethylcellulose (Step b) of the Method)

(2 a) The carboxymethylcellulose methyl ester (30 g), obtained by the method of Section (1 a), is heated under reflux with stirring for 6 hours with 200 g of dimethylaminopropylamine. The reaction mixture is cooled and 1,000 g of isopropanol are added for the complete precipitation of the reaction product. The carboxymethylcellulose aminamide is isolated by filtering with the help of suction and extracted with isopropanol in a Soxhlet apparatus. The amine nitrogen content of the product is determined by titration to be 2.2%. This corresponds to a 60% conversion. The product is readily soluble in water.

(2 b) Carboxymethylcellulose methyl ester (30 g), obtained according to the method of Section 1 a), is heated in a 250 mL laboratory autoclave together with 24 g of dimethylaminopropylamine and 100 g of methanol with stirring for 1 hour at 150° C., a pressure of 18 bar developing. After cooling, the product is filtered off with suction and washed with methanol. The amine nitrogen content after drying is determined by titration to be 3.4%. This corresponds to a 92% conversion based on the ester groups. The $^1$H-NMR spectrum, recorded in $D_2O$, shows the signal of the methyl substituent of the tertiary amino group at 2.4 ppm as the characteristic peak.

(2 c) As described in Section 2 b), 30 g of the same carboxymethylcellulose methyl ester are reacted with 21 g of dimethylaminoethylamine. The amine nitrogen content of the carboxymethylcellulose aminamide obtained is determined by titration to be 3.3%. This corresponds to an 85% conversion of the ester groups.

2 d) In the same way, 30 g of the same carboxymethylcellulose methyl ester are reacted with 24 g of N,N,N'-trimethylethylenediamine. The amine nitrogen content of the carboxymethylcellulose aminamide obtained is determined by titration to be 2.9%. This corresponds to a 79% conversion of the ester groups.

2 e) In the same way, 30 g of the same carboxymethylcellulose methyl ester are reacted with 37 g of 1-diethylamino-4-aminopentane. The amine nitrogen content of the carboxymethylcellulose aminamide obtained is determined by titration to be 2.6%. This corresponds to a 83% conversion of the ester groups.

2 f) In the same way, 30 g of the same carboxymethylcellulose methyl ester are reacted with 40 g of dibutylaminoethylamine. The amine nitrogen content of the carboxymethylcellulose aminamide obtained is determined by titration to be 2.4%. This corresponds to an 80% conversion of the ester groups.

2 g) The carboxymethylcellulose methyl ester (30 g), obtained according to the method of Section 1 b), is heated with stirring for 1 hour at 150° C. in a 250 mL laboratory autoclave together with 24 g of dimethylaminopropylamine and 100 g of isopropanol, a pressure of about 10 bar developing. After cooling, the product is filtered off with suction and washed with isopropanol. The amine nitrogen content after drying is determined by titration to be 2.4%. This corresponds to a 65% conversion of the ester groups. The Brookfield viscosity of a 2% aqueous solution of the carboxymethylcellulose aminamide prepared is 500 mPas.

3. Quaternization of the Aminamide of the Carboxymethylcellulose (Step c) of the Method)

3 a) The carboxymethylcellulose aminamide (25 g), obtained by the method of Section 2 b), is suspended in 400 ml of methanol. Chloromethane is passed slowly into the suspension at room temperature, until it is no longer absorbed. This can easily be determined by the condensation of the excess chloromethane in a downstream cold trap. The reaction is concluded after about 5 hours. The product is filtered off with suction. In the quaternary ammonium derivative of cellulose obtained, the amine nitrogen is no longer detectable unambiguously by titration of an aqueous solution of the polymer with perchloric acid. The chloride content is 7.2%. The $^1$H-NMR spectrum, recorded in $D_2O$, shows as characteristic peaks the signals of the methyl substituents of the tertiary amino group at 2.9 ppm and of the quaternary ammonium group at 3.2 ppm. The intensity ratio of these signals indicates an approximately 90% conversion. Starting out from a carboxymethylcellulose with a degree of substitution DS=0.9, a 90% conversion during the esterification reaction and a 92% conversion during the amidation reaction, a degree of substitution DS=approx. 0.67, based on the quaternary groups, is obtained.

3 b) As described in Section 3 a), 25 g of carboxymethylcellulose aminamide, the synthesis of which is described in Section 2 c), is reacted with chloromethane. In the quaternary ammonium derivative of cellulose obtained, the amine nitrogen can no longer be detected unambiguously by titration with perchloric acid. The chloride content of the product is 6.8%.

3 c) As described in Section 3 a), 25 g of cellulose aminamide, the synthesis of which is described in Section 2 d), is reacted with chloromethane. In the quaternary ammonium derivative of cellulose obtained, the amine nitrogen can no longer be detected unambiguously by titration with perchloric acid. The chloride content of the product is 6%.

3 d) Carboxymethylcellulose aminamide (25 g), the synthesis of which is described in Section 2 e), and 120 mL of methanol are placed in a 250 mL laboratory autoclave. Chloromethane (6 g) is passed in and condensed. The temperature is subsequently raised for 5 hours to 80° C. After cooling, the excess chloromethane and a portion of the methanol are removed under reduced pressure. The product is filtered off and dried. The amine nitrogen can no longer be detected unambiguously by titration with perchloric acid; the chloride content is 5.5%.

3 e) As described in Section 3 d), 25 g of carboxymethylcellulose aminamide, the synthesis of which is described in Section 2 f), is quaternized with an excess of chloromethane. The chloride content is 4.6%.

3 f) Carboxymethylcellulose aminamide (25 g), the synthesis of which is described in Section 2 b), is suspended in 300 mL of a solvent, consisting of 9 parts of isopropanol and 1 part of water, mixed with 36.6 g of butyl bromide and heated for 5 hours at 60° C. with intensive stirring. After cooling, the product is filtered off, washed with isopropanol and dried. The bromide content is 12.5%.

3 g) Carboxymethylcellulose aminamide (25 g), the synthesis of which is described in Section 2 b), is suspended in 300 mL of solvent, consisting of 9 parts of isopropanol and 1 part of water, mixed with 33.8 g of benzyl chloride and heated for 5 hours at 60° C. with intensive stirring. After cooling, the product is filtered off, washed with isopropanol and dried. The chloride content is 6.8%.

3 h) Carboxymethylcellulose aminamide (25 g), the synthesis of which is described in Section 2 b), is suspended in 300 mL of solvent, consisting of 9 parts of isopropanol and 1 part of water, mixed with 41 g of diethyl sulfate and heated for 8 hours at 60° C. with intensive stirring. After cooling, the product is filtered off, washed with isopropanol and dried. The $^1$H-NMR spectrum, recorded in $D_2O$, shows the signals of the methyl substituents of the tertiary amino group at 2.9 ppm and of the quaternary ammonium group at 3.2 ppm as characteristic peaks. The intensity ratio of these signals indicate an approximately 80% conversion.

II. Investigation of the dissolving behavior of inventive quaternary cellulose derivatives in water in comparison with other quaternary cellulose derivatives of the state of the art The dissolving behavior of the following quaternary cellulose derivatives is investigated:

A: A hydroxyethylcellulose of low viscosity, modified with 3-chloro-2-hydroxypropyltrimethylammonium chloride, corresponding to the German Patent No. 1,593,657. The product has a nitrogen content of 1.7% and is commercially available under the name of Polymer JR 400.

B: A hydroxyethylcellulose of higher viscosity, modified with 3-chloro- 2-hydroxypropyltrimethylammonium chloride, corresponding to the German Patent No. 1,593,657. The product has a nitrogen content of 1.7% and is commercially available under the name of Polymer JR 30 M.

C: A cellulose, modified with glycide and subsequently with 3-chloro-2-hydroxypropyltrimethylammonium chloride, corresponding to Example S 7 of the German Offenlegungsschrift No. 3,301,667. The product has a nitrogen content of 2.2%.

D: An inventive, quaternary cellulose derivative containing quaternary ammonium groups. Its synthesis is described in Section 3 a).

In each case, 1 g of the cellulose derivatives A, B, C and D is added, while stirring with a magnetic stirrer (approximately 300 rpm) to 99 g of water at 20° C. The time required for complete dissolution of the products is measured. The solutions formed are evaluated with respect to their nature. The results are summarized in the following Table:

| Product | Time to Complete Dissolution of [min] | Nature of the Solution | Brookfield Viscosity of the Solution [mPas] |
|---|---|---|---|
| A | 75 | clear | 400 |
| B | 75 | clear | 1200 |
| C | >75 | cloudy | 100 |
| D | 20 | clear | 300 |

III

1. Treatment of hair with inventive quaternary cellulose derivatives and quaternary cellulose derivatives of the state of the art From each of the quaternary derivatives A, B and C, which correspond to the state of the art, and from each of five different quaternary cellulose derivatives, 0.1% by weight aqueous solutions are prepared. For the sake of simplicity, the inventive quaternary cellulose derivatives are named as follows:

D: the synthesis of which is described in Section 3 a)
E: the synthesis of which is described in Section 3 b)
F: the synthesis of which is described in Section 3 c)
G: the synthesis of which is described in Section 3 d)
H: the synthesis of which is described in Section 3 g)

The aqueous solutions of cellulose derivatives A, B and C, which are not of the invention, are described in Section II.

Chinese fine hair, 15 cm long, is bleached with a commercial bleach for 1 hour according to the directions provided and subsequently dried. The care rinse, enclosed with the bleaching agent, is not used. The now lightened and damaged hair is tied into strands of about 1 g each. The strands are left for 10 minutes at 30° C. in the solutions described above. Subsequently, they are rinsed thoroughly for 3 minutes in lukewarm running water, dried for 12 hours in air and combed. In each case, 3 strands of hair are treated with each of the solutions.

The gloss of the treated hair strands generally is clearly improved and good to very good. With regard to handle and combability, there are clear differences between the differently treated strands of hair. On the basis of these differences, the cellulose derivatives A to H can be arranged in a sequence. The cellulose derivatives, which lead to the best result, are named first. The following results are obtained:

Wet Combability: E>D>F>A=H>G>C=B>> bleached, untreated hair

Dry Combability: H=D>F>E>G>C>B>A>> bleached, untreated hair

Handle: E>D>G>H>C=F>B>A>> bleached, untreated hair

According to these results, the inventive compounds D and E proved to be particularly suitable for this application.

2. Treatment of hair with shampoo preparations, which contain inventive quaternary cellulose preparations and quaternary cellulose derivatives of the state of the art With the quaternary cellulose derivatives A to H, described in the preceding Section, shampoo preparation are produced, which consist of 1% cellulose derivative, 20% sodium lauryl sulfate, 4% sodium chloride and 75% water.

Chinese fine hair is bleached and tied into strands as described.

For the treatment, the hair strands are immersed for 10 minutes at 20° C. in the shampoo preparations diluted with 9 parts of water, then rinsed thoroughly for 3 minutes with luke-warm, running water, dried in air for 12 hours and combed. In each case, 3 hair strands are treated with each of the shampoo solutions.

The gloss of the treated hair strands generally is clearly improved and good to very good. With regard to handle and combability, there are clear differences. The following results are obtained:

Wet Combability: E>D>F=H=G=A>C>B>> bleached, untreated hair
Dry Combability: H>G>E>D>C>F>B>A>> bleached, untreated hair
Handle: E>D>G>C>F>H>B>A>> bleached, untreated hair The shampoo preparations, prepared with the cellulose derivatives C, D, E and G, result in hair with a particularly pleasant handle; However, cellulose derivative C also brings about an increased static friction (adhesiveness). The shampoo preparations produced with other cellulose derivatives, bring about a handle, which is less smooth and less soft; however, the handle of these hairs is clearly improved in comparison with that of untreated hair.

I claim:

1. A quaternary ammonium group containing carboxymethylcellulose derivative wherein at least a portion of the sites normally occupied by carboxymethyl groups are occupied by quaternary ammonium groups of the general formula

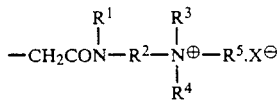

wherein
 $R^1$ is hydrogen or methyl,
 $R^2$ is a divalent aliphatic hydrocarbon group with 2 to 5 carbon atoms,
 $R^3$, $R^4$ are alkyl with 1 to 4 carbon atoms,
 $R^5$ is alkyl with 1 to 4 carbon atoms or benzyl,
 X is halogen, sulfate ester group or a sulfonic acid group,
with the proviso that, on the average, at least 0.1 quaternary ammonium groups are present for each anhydroglucose unit of the polymeric molecule.

2. A tertiary amino group containing carboxymethylcellulose derivative wherein at least a portion of the sites normally occupied by carboxymethyl groups are occupied by tertiary amino groups of the general formula

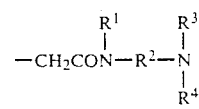

wherein
 $R^1$ is hydrogen or methyl,
 $R^2$ is a divalent aliphatic hydrocarbon group with 2 to 5 carbon atoms,
 $R^3$, $R^4$ are alkyl with 1 to 4 carbon atoms,
with the proviso that, on the average, at least 0.1 tertiary amino groups are contained per anhydroglucose unit of the polymeric molecule.

3. A method for the synthesis of a quaternary ammonium group containing carboxymethylcellulose derivative comprising:
 (a) esterifying the alkali salt of a carboxymethylcellulose at temperatures of about between 80° to 170° C., a pressure of about between 5 to 100 bar and a reaction time of about between 1 to 24 hours with, based on the carboxymethyl groups, a 1- to 10-fold molar excess of alkyl chloride, the alkyl group of which has 1 to 3 carbon atoms;
 (b) removing after the esterification excess alkyl chloride from the reaction mixture;
 (c) reacting the ester of the carboxymethylcellulose thus obtained with an amine of the general formula

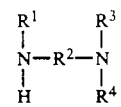

in which $R^1$, $R^2$, $R^3$ and $R^4$ have the above meaning, at temperatures of between about 80° to 150° C. and a reaction time of between about 1 to 10 hours in such amounts that 1 to 10 moles of amine are present per mole of ester group;
 (d) removing the excess amine after the reaction from the reaction mixture; and
 (e) reacting the derivative of carboxymethylcellulose thus obtained and containing tertiary amino groups for between about 0.5 to 8 hours with, based on the tertiary amino groups, at least equimolar amounts of the compound $R^5$—X, wherein
  $R^5$ is alkyl with 1 to 4 carbon atoms or benzyl,
  X is halogen, sulfate ester group or a sulfonic acid group.

4. A preparation comprising an aqueous vehicle and the carboxymethylcellulose derivative of claim 1 in an amount of about 0.1 to 2.5% by weight.

5. A hair care preparation having the composition of claim 4.

6. A method of treating hair, which comprises applying to hair the preparation of claim 4.

7. The quaternary ammonium group containing carboxymethylcellulose derivative according to claim 1, in which 0.3 to 0.8 of the quaternary ammonium groups are present for each anhydroglucose unit of the polymeric molecule.

8. The quaternary ammonium group containing carboxymethylcellulose derivative according to claim 1, in which 0.3 to 0.6 of the quaternary ammonium groups are present for each anhydroglucose unit of the polymeric molecule.

9. The quaternary ammonium group containing carboxymethylcellulose derivative according to claim 1, which contains about 400 to 10,000 anhydroglucose units in the average polymeric molecule.

10. The tertiary amino group containing carboxymethylcellulose derivative according to claim 2, in which 0.3 to 0.8 of the tertiary amino groups are contained for each anhydroglucose unit of the polymeric molecule.

11. The tertiary amino group containing carboxymethylcellulose derivative according to claim 2, in which 0.3 to 0.6 of the tertiary amino groups are present for each anhydroglucose unit of the polymeric molecule.

12. The tertiary amino group containing carboxymethylcellulose derivative according to claim 2, which contains about 400 to 10,000 anhydroglucose units in the average polymeric molecule.

* * * * *